United States Patent [19]

Pedersen et al.

[11] Patent Number: 4,749,810

[45] Date of Patent: Jun. 7, 1988

[54] STRONG ACID HYDROCARBOXYLATION OF PROPYLENE TO ISOBUTYRIC ACID USING METAL PHTHALOCYANINES AS CO-CATALYSTS

[75] Inventors: S. Erik Pedersen, Mentor; Frederick A. Pesa, Aurora; Thomas A. Haase, University Heights, all of Ohio

[73] Assignee: The Standard Oil Company, Cleveland, Ohio

[21] Appl. No.: 206,818

[22] Filed: Nov. 14, 1980

[51] Int. Cl.$^4$ .................... C07C 51/14; C07C 57/04
[52] U.S. Cl. .................... 562/521; 562/522
[58] Field of Search .................... 562/521, 522

[56] References Cited

U.S. PATENT DOCUMENTS

| | | | |
|---|---|---|---|
| 2,022,244 | 11/1935 | Larson | 562/521 |
| 2,768,968 | 10/1956 | Reppe et al. | 562/522 |
| 3,047,622 | 7/1962 | Kurhajec et al. | 562/521 |
| 3,059,004 | 10/1962 | Waabe et al. | 562/521 |
| 3,116,328 | 12/1963 | Cox et al. | |
| 3,450,730 | 6/1969 | Scheben et al. | 562/522 |
| 3,910,963 | 10/1975 | Souma et al. | 562/522 |
| 4,039,564 | 8/1977 | Schmerling et al. | 562/521 |
| 4,039,585 | 8/1977 | Homeier | 568/909 |
| 4,100,359 | 7/1978 | Schmerling et al. | 562/519 |
| 4,158,572 | 6/1979 | Blackburn et al. | 6/288 |
| 4,168,245 | 9/1979 | Carlson et al. | 252/431 |
| 4,234,455 | 11/1980 | Homeier et al. | 252/430 |

OTHER PUBLICATIONS

Bregeault et al., Metal Carbonyl Cations in Sulfuric Acid . . . , Hexene, J. Molecular Catalysis 4, (1978), pp. 225–229.

Primary Examiner—Vivian Garner
Attorney, Agent, or Firm—M. F. Esposito; J. G. Curatolo; L. W. Evans

[57] ABSTRACT

A process for the selective hydrocarboxylation of propylene to produce predominantly isobutyric acid in the liquid phase is provided. The reaction of propylene, carbon monoxide and water is effected at a temperature of about 10° C. to about 80° C. and at a pressure of about 75 psi to about 1500 psi in the presence of a strong acid and a metal phthalocyanine co-catalyst.

9 Claims, No Drawings

STRONG ACID HYDROCARBOXYLATION OF PROPYLENE TO ISOBUTYRIC ACID USING METAL PHTHALOCYANINES AS CO-CATALYSTS

BACKGROUND OF THE INVENTION

This invention relates to the hydrocarboxylation of olefins to form carboxylic acids. More specifically, this invention relates to the hydrocarboxylation of propylene with carbon monoxide and water in the liquid phase to produce isobutyric acid. The branched isomer of butyric acid is desired as it may be dehydrogenated to produce methacrylic acid.

Carboxylic acids have previously been synthesized from olefins, carbon monoxide and water in strong acids. However, temperatures in excess of 100° C. and pressures in excess of 500 atmospheres were required to achieve satisfactory yields. Milder conditions could be used if the olefin and carbon monoxide were pre-reacted in a substantially anhydrous strong acid prior to the reaction with the required amount of water. Olefin polymerization is a competing reaction which lowers the selectivity of the hydrocarboxylation reaction to the desired carboxylic acid product.

U.S. Pat. No. 3,910,963 describes the hydrocarboxylation of olefins in sulfuric acid using co-catalysts comprising Group IIB metal ions. The reaction is greatly inhibited by excess water.

Hydroformylation catalysts comprising cobalt carbonyl and porphyrin promoter ligands are described in U.S.S.N. 104,644, filed Dec. 17, 1979, assigned to our common assignee.

Bregeault et al., "Metal Carbonyl Cations in Sulphuric Acid as Catalysts for Carboxylation Reactions of Hexanol and Hexene", *Journal of Molecular Catalysis*, 4 (1978) pages 225–229, discloses the carboxylation of 2 hexanol in concentrated sulfuric acid using a tetraprotonated phthalocyanineiron (Table 1 on page 227) to yield a mixture of carboxylic acids having from 5 to 8 carbon atoms.

U.S. Pat. No. 3,116,328 describes the preparation of hydrocarbon substitued thiuramdisulfide in the presence of a metal phthalocyanine catalyst at a pH of 7 to 12. U.S. Pat. No. 4,168,245 discloses the use of metal phthalocyanines for the treatment of petroleum distillates boiling in excess of 135° C.

The rate of the strong acid catalyzed hydrocarboxylation reaction is relatively slow. Transition metal catalyzed hydrocarboxylation reactions conducted in organic solvent demonstrate increased rates of reaction, but lower the selectivity of the reaction such that the straight-chained carboxylic acid isomer is produced.

SUMMARY OF THE INVENTION

It is therefore an object of the present invention to provide a process for the hydrocarboxylation of propylene in the liquid phase to produce isobutyric acid.

It is a further object of the present invention to provide a process for the hydrocarboxylation of propylene in the liquid phase using a co-catalyst system of a strong acid and a metal phthalocyanine to produce predominantly the branched-chain isomer of butyric acid.

It is a further object of the present invention to provide a process for the hydrocarboxylation of propylene in the liquid phase using a co-catalyst system of strong acid and a metal phthalocyanine wherein the rate of reaction is enhanced.

These and other objects of the present invention, together with the advantages thereof, which shall become apparent from the specification which follows, are accomplished by the invention as hereinafter described and claimed.

In general, the process of the present invention includes the preparation of isobutyric acid in the liquid phase. A reaction mixture is formed from propylene, carbon monoxide and water in a strong acid in the presence of a metal phthalocyanine co-catalyst. The reaction mixture is subjected to temperatures of about 10° C. to about 80° C. and pressures of about 15 psi to about 1500 psi.

DETAILED DESCRIPTION OF THE INVENTION

The preparation of the iso or branched isomer of butyric acid from propylene, carbon monoxide and water in the liquid phase proceeds according to the following reaction.

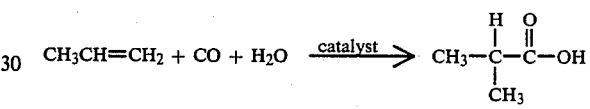

The formation of n-butyric acid, in which all the carbon atoms form a straight chain, is desired to be minimized to the greatest extent possible.

When the reactants propylene, carbon monoxide and water are contacted in a reaction mixture which contains a strong acid, the selectivity for the branched acid product is excellent. We have found that the use of a metal phthalocyanine co-catalyst, together with a strong acid, increases the reaction rate for the formation of isobutyric acid without adversely affecting the selectivity.

The reaction mixture, according to the process of the present invention, comprises a concentrated aqueous solution of a strong acid or a mixture of strong acids, including but not limited to $H_2SO_4$, $H_3PO_4$, HF, $HSO_3F$, $CF_3SO_3H$, $HF/BF_3$, $H_3PO_4/BF_3$, BF thereof. Sulfuric acid is preferred. The molar concentration of the acid in water should be within the range of about 87% to about 98%, with about 92% being preferred.

In the reaction mixture, the molar ratio of the strong acid to propylene should be above about 4:1, lower ratios favoring the polymerization of propylene. Preferred molar ratios of strong acid to propylene are about 4:1 to about 16:1.

The metal phthalocyanine compound which serves as a co-catalyst for the preparation of isobutyric acid according to the process of the present invention is represented by the following structure

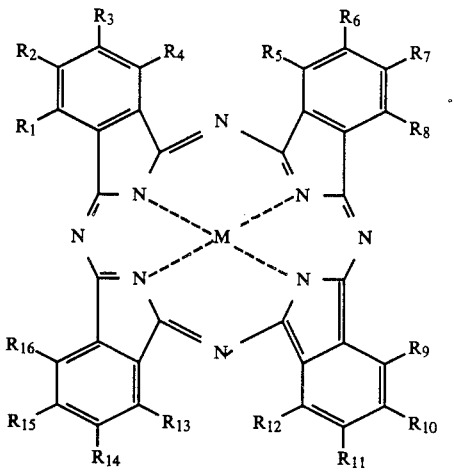

wherein M is selected from the group consisting of V, Mn, Co, Ni and Cu, and wherein $R_1$ throug $R_{16}$ are each independently selected from
 (a) H
 (b) alkyl groups having from one to about 12 carbon atoms
 (c) fluorine-substituted alkyl groups having from one to about 12 carbon atoms
 (d)

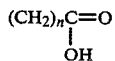

wherein n=0 to about 12.

Preferred are metal phthalocyanines wherein the metal is selected from Co, Ni and Cu.

Metal phthalocyanines are commercially available and may be prepared according to known methods. The metal phthalocyanine co-catalyst is soluble in the concentrated strong acid containing reaction mixture. The molar ratio of the metal phthalocyanine co-catalyst to the strong acid present in the reaction mixture should be in the range of about 0.01:1 to about 1:1.

The reaction of propylene, carbon monoxide and water in the reaction mixture comprising the strong acid and the metal phthalocyanine co-catalyst should be conducted at a temperature in the range of about 10° C. to about 80° C. Reaction at a higher temperature results in a decrease in selectivity due to the polymerization of the propylene. Preferred temepratures are in the range of about 15° C. to about 45° C.

The molar ratio of water to propylene in the reaction medium should be maintained within the range of about 0.01:1 to about 2:1. It is preferred that the molar ratio of water to propylene be maintained at about 0.1:1 to about 1:1.

The reaction should be carried out under a carbon monoxide pressure of about 75 psi to about 1500 psi. Preferred carbon monoxide pressures are about 150 psi to about 500 psi.

After reaction is completed, the isobutyric product may be separated from the reaction mixture by convention methods, such as distillation. The metal phthalocyanine co-catalyst, being insoluble in aqueous media other than concentrated strong acids, can be separated from the reaction mixture by filtration after the addition of a large amount of water, such as would occur after the hydrolysis step in a batch reaction. The metal co-catalyst could then be recycled together with the strong acid-containing reaction mixture after distillation for use in a subsequent hydrocarboxylation reaction.

SPECIFIC EMBODIMENTS OF THE INVENTION

A series of exempletive reactions were carried out in a 300 ml Hastelloy C autoclave. Although the examples were carried out as batch type reactions to illustrate the invention, it is intended that the scope of the present invention include continuous feed-type reactions also.

Analysis of the liquid reaction product was performed on a Hewlett Packard 5710A gas chromatograph. Valeric acid was used as the internal standard and column packing was Polyester FF (trademark of Nishio Industries). Analysis of gases was performed on a Carle III gas analyzer using a Houdry dual column with thermisters as detectors.

EXAMPLES 1-6 AND COMPARATIVE A

The reactions in Examples 1-6 and Comparative Example A were carried out in the following manner. To the autoclave was added 115 ml of the strong acid, 96% $H_2SO_4$, together with a pre-weighed amount of metal phthalocyanine co-catalyst. The autoclave was flushed twice with 100 psi of carbon monoxide, was pressurized to 150 psi of carbon monoxide and was maintained at 25° C. for one hour with agitation. The autoclave pressure was reduced to 90 psi and a pre-weighed amount of propylene (liquid) was added. The autoclave was then pressured to the desired reaction pressure, the temperature was increased to 40° C. and the reaction was carried out for one hour at constant pressure. After the one hour reaction, the autoclave was cooled, the gases vented and analyzed, the solution quenched with $H_2O$ and the liquid effluent weighed and analyzed as set forth above.

The results of the above reaction runs (yields) together with the type and amount of metal phthalocyanine co-catalyst, amount of propylene charged, and reaction pressure used are set forth in Table I. Yield was calculated as moles of isobutyric acid produced times 100, divided by moles of propylene charged.

TABLE I

| | Hydrocarboxylation of Propylene in $H_2SO_4$ (96%) | | | |
|---|---|---|---|---|
| Example | Metal Phthalocyanine Co-Catalyst | CO Pressure (psi) | Propylene grams | % Yield |
| 1 | Vanadium (7.4 g) | 200 | 2.9 | 32 |
| 2 | Manganese (7.4 g) | 150 | 1.9 | 41 |
| 3 | Copper (7.5 g) | 150 | 2.5 | 66 |
| 4 | Nickel (7.4 g) | 200 | 2.8 | 83 |
| 5 | Cobalt (3.7 g) | 200 | 2.2 | 89.9 |
| 6 | Cobalt (3.7 g) | 200 | 1.8 | 78 |
| Comparative A (no co-catalyst)* | | 200 | 2.7 | 54.6 |

*98% $H_2SO_4$ only

EXAMPLES 7-12 AND COMPARATIVE B

Reactions in Examples 7-12 and Comparative B were carried out in the following manner. To the autoclave was added 150 ml of the desired concentration of the strong acid $H_2SO_4$ together with a pre-weighed amount of metal phthalocyanine co-catalyst. The autoclave was flushed twice with 100 psi of carbon monoxide, pressurized to 200 psi, cooled to the desired reaction temperature and the reaction mixture was stirred for about one-half hour. After this "prerun", the pressure was reduced to one atmosphere carbon monoxide and a pre-weighed amount of propylene (liquid) was added. The pressure was increased to 500 psi or the reaction run pressure desired, the temperature increased to run temperature and the carbon monoxide pressure drop was monitored. Pressure drop was measured by attaching a pressure transducer to a 1.65 liter CO reservoir from which gases were regulated at constant pressure to the autoclave. Pressure drop was followed and recorded on a millivolt recorder attached to the pressure transducer.

The reaction was allowed to run 24 hours, during which time pressure drop was completed. The autoclave was cooled, gases analyzed and the liquid effluent was weighed and analyzed.

Results of the above reaction runs (yields) together with the concentration of H₂SO₄, type and amount of metal phthalocyanine co-catalyst, amount of propylene charged, reaction pressure, time and temperature are reported in Table II.

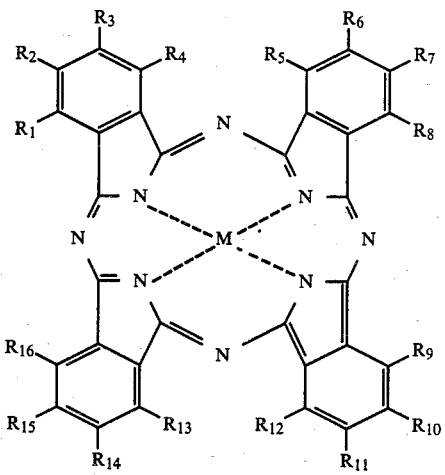

wherein M is selected from V, Mn, and Cu and wherein $R_1$ through $R_{16}$ are each independently selected from

TABLE II

| | | Hydrocarboxylation of Propylene | | | | | |
|---|---|---|---|---|---|---|---|
| Ex. No. | Metal Phthalocyanine | % H₂SO₄ | Temp. (°C.) | Press. (PSI) | Grams Propylene | Reaction Time (Min.) | % Yield |
| Comp. B | — | 92 | 15 | 500 | 13.26 | 1500 | 62.7 |
| 7 | Nickel (3.7 g) | 92 | 15 | 500 | 14.35 | 1440 | 87.5 |
| 8 | Nickel (22.9 g) | 92 | 20 | 500 | 14.09 | 1440 | 87.6 |
| 9 | Nickel (3.7 g) | 96 | 25 | 200 | 8.09 | 240 | 43.1 |
| 10 | Cobalt (3.7 g) | 96 | 25 | 900 | 8.10 | 180 | 28.4 |
| 11 | Cobalt (3.7 g) | 96 | 25 | 1500 | 7.74 | 60 | 27.6 |
| 12 | Cobalt (3.7 g) | 92 | 15 | 500 | 14.42 | 1260 | 44.5 |

Although propylene was added to the reaction mixture in liquid form in the above examples in order to permit accurate measurements, addition of propylene in the gaseous form is preferred. The butyric acid produced by the process of the present invention is essentially all branched isomer. No straight-chain, n-butyric acid was detected.

Thus it should be apparent to those skilled in the art that the subject invention accomplishes the objects set forth above. It is to be understood that the subject invention is not to be limited by the examples set forth herein. These have been provided merely to demonstrate operability and the selection of strong acids, metal phthalocyanine co-catalysts, and reaction conditions can be determined by the total specification disclosure provided without departing from the spirit of the invention herein disclosed and described, the scope of the invention including modifications and variations that fall in the scope of the attached claims.

We claim:

1. A process for the selective hydrocarboxylation of propylene to produce isobutyric acid in the liquid phase at a temperature of about 10° C. to about 80° C. and a pressure of about 15 psi to about 1500 psi comprising forming a reaction mixture of propylene, carbon monoxide and water in a concentrated strong acid in the presence of a co-catalyst consisting essentially of a metal phthalocyanine compound represented by the structure:

(a) H
(b) alkyl groups having from one to about 12 carbon atoms
(c) fluorine-substituted alkyl groups having from one to about 12 carbon atoms
(d)

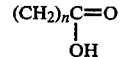

wherein n=0 to about 12.

2. The process of claim 1 wherein said strong acid is selected from H₂SO₄, H₃PO₄, HSO₃F, CF₃SO₃H, BF₃, SbF₅ and mixtures thereof.

3. The process of claim 1 wherein said strong acid is H₂SO₄.

4. The process of claim 1 wherein the strong acid molar concentration in water is about 87% to about 98%.

5. The process of claim 1 wherein said reaction temperature is about 15° C. to about 45° C.

6. The process of claim 1 wherein the reaction pressure is about 150 psi to about 500 psi.

7. The process of claim 1 wherein the molar ratio of said strong acid to propylene is above about 4:1.

8. The process of claim 1 wherein the molar ratio of said metal phthalocyanine compound to said strong acid is about 0.01:1 to about 1:1.

9. The process of claim 1 wherein the molar ratio of water to propylene is about 0.1:1 to about 2:1.

* * * * *